United States Patent
Lupton

(10) Patent No.: US 8,262,589 B2
(45) Date of Patent: Sep. 11, 2012

(54) GUIDE WIRE FOR USE WITH A CATHETER

(75) Inventor: Henry William Lupton, Oranmore (IE)

(73) Assignee: Brivant Research & Development Limited, Galway (IE)

( * ) Notice: Subject to any disclaimer, the term of this patent is extended or adjusted under 35 U.S.C. 154(b) by 34 days.

(21) Appl. No.: 12/850,838

(22) Filed: Aug. 5, 2010

(65) Prior Publication Data
US 2010/0324539 A1 Dec. 23, 2010

Related U.S. Application Data

(62) Division of application No. 10/567,459, filed as application No. PCT/IE2004/000107 on Aug. 9, 2004, now Pat. No. 7,789,839.

(30) Foreign Application Priority Data

Aug. 7, 2003 (IE) .................................. S2003/0585

(51) Int. Cl.
*A61M 25/00* (2006.01)
*A61M 25/01* (2006.01)
*A61M 25/02* (2006.01)
(52) U.S. Cl. ...................................................... 600/585
(58) Field of Classification Search .................... 600/585
See application file for complete search history.

(56) References Cited

U.S. PATENT DOCUMENTS

| | | | | |
|---|---|---|---|---|
| 3,500,820 A | * | 3/1970 | Almen | 600/434 |
| 4,846,186 A | * | 7/1989 | Box et al. | 600/434 |
| 5,365,942 A | * | 11/1994 | Shank | 600/585 |
| 5,372,144 A | * | 12/1994 | Mortier et al. | 600/585 |
| 5,957,865 A | * | 9/1999 | Backman et al. | 600/585 |

(Continued)

FOREIGN PATENT DOCUMENTS

| | | |
|---|---|---|
| EP | 0773037 | 5/1997 |
| WO | 0040288 | 7/2000 |

OTHER PUBLICATIONS

International Search Report for PCT App. No. PCT/IE2004/000107 mailed on Oct. 28, 2004.

(Continued)

*Primary Examiner* — Sean Dougherty
(74) *Attorney, Agent, or Firm* — Whyte Hirschboeck Dudek S.C.; Grady J. Frenchick

(57) ABSTRACT

A guide wire (1) for use with a catheter for accessing a remote site in the venal or other system of the body of a human or animal subject comprises a core wire (2) extending from a proximal end (5) to a distal end (6). The core wire (2) terminates at the distal end (6) in a distal portion (16) which is of rectangular transverse cross-section defining a pair of opposite major surfaces (18,19) and minor surfaces (20,21). The distal portion (16) also defines a central major plane (24) which lies between the major surfaces (18,19) and bisects the minor surfaces (20,21), and a central minor plane (25) which lies between the minor surfaces (20,21) and bisects the major surfaces (18,19). An alignment portion (27) for aligning the distal end (6) with a branched vessel of the vascular system is formed in the distal portion (16) by bending the distal portion (16) in the central major plane 24 to form a curved portion (28) from which the alignment portion (27) extends, the curved portion 28 and the alignment portion 27 lying in the central minor plane 24. By bending the distal portion (16) in its central major plane, the column strength of the guide wire (1) is such as to minimize the danger of buckling of the distal portion in the central minor plane (25).

16 Claims, 11 Drawing Sheets

U.S. PATENT DOCUMENTS

Figure 3:
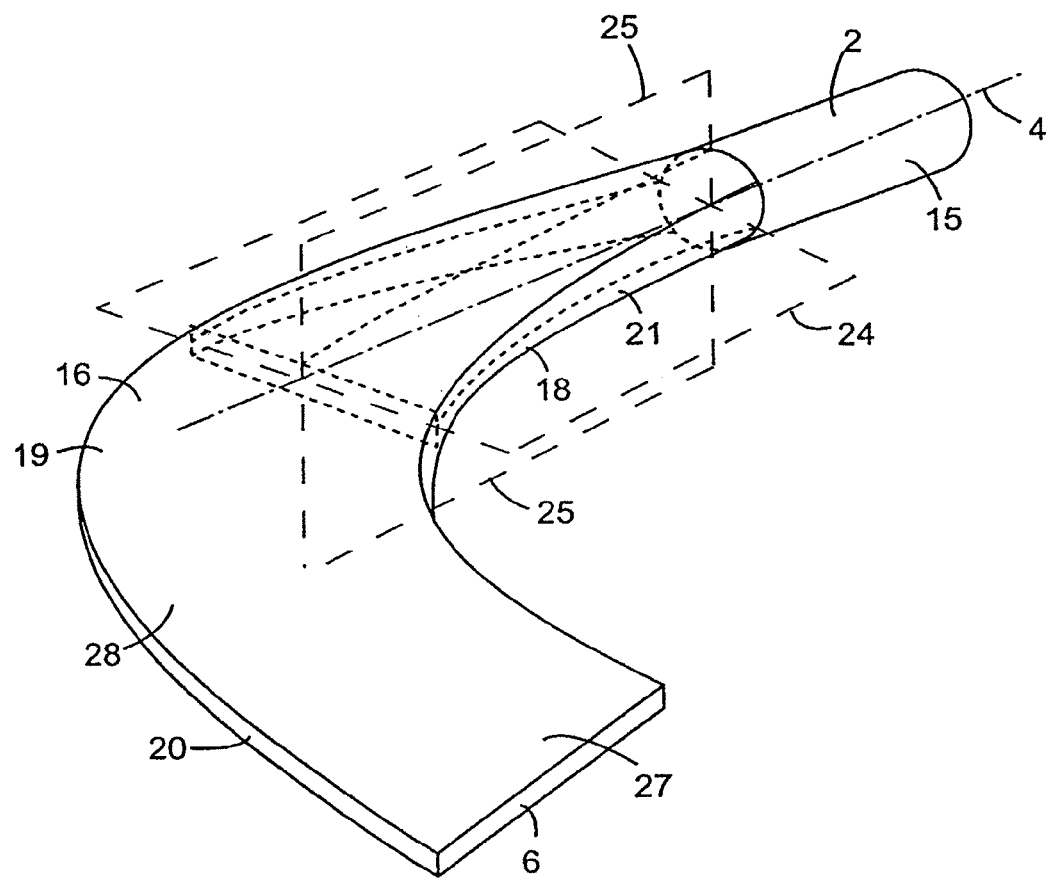

| | | | |
|---|---|---|---|
| 6,146,339 A * | 11/2000 | Biagtan et al. | 600/585 |
| 6,575,920 B2 * | 6/2003 | Zhou | 600/585 |
| 6,652,472 B2 * | 11/2003 | Jafari et al. | 600/585 |
| 7,128,718 B2 * | 10/2006 | Hojeibane et al. | 600/585 |
| 7,399,283 B2 * | 7/2008 | Kato | 600/585 |
| 2002/0082523 A1 * | 6/2002 | Kinsella et al. | 600/585 |
| 2002/0091338 A1 * | 7/2002 | Frautschi | 600/585 |
| 2003/0013993 A1 * | 1/2003 | Jafari et al. | 600/585 |

OTHER PUBLICATIONS

EP Office Action for EP App. No. 04744858.4 mailed on Sep. 5, 2007.

EP Office Action for EP App. No. 04744858.4 mailed on Dec. 5, 2008.

JP Office Action for JP App. No. 06/0522490 mailed 2010-03-00.

* cited by examiner

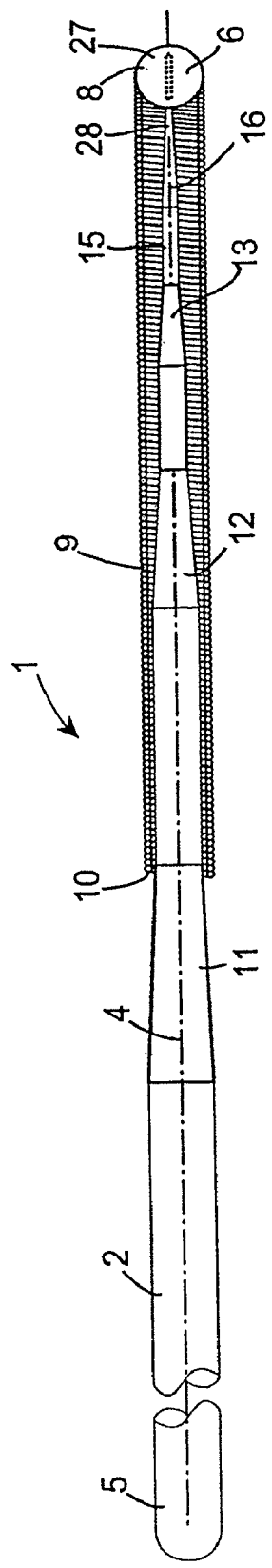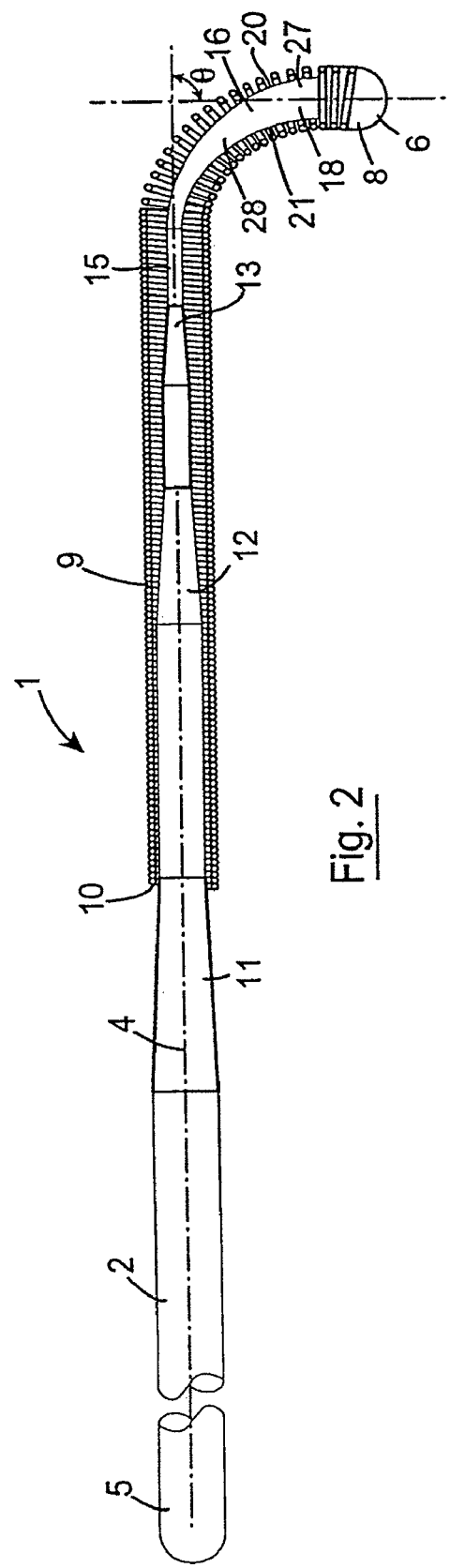

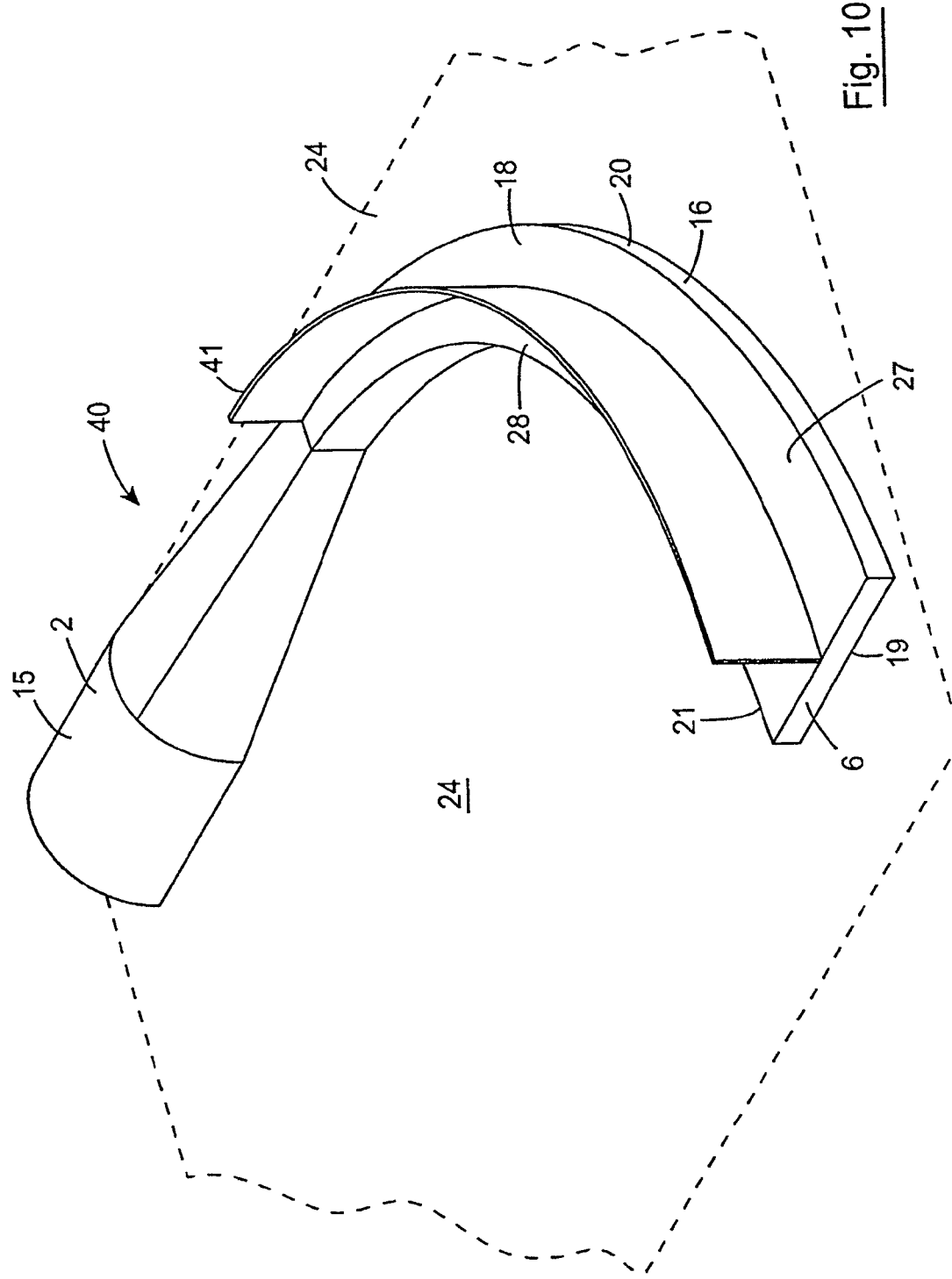

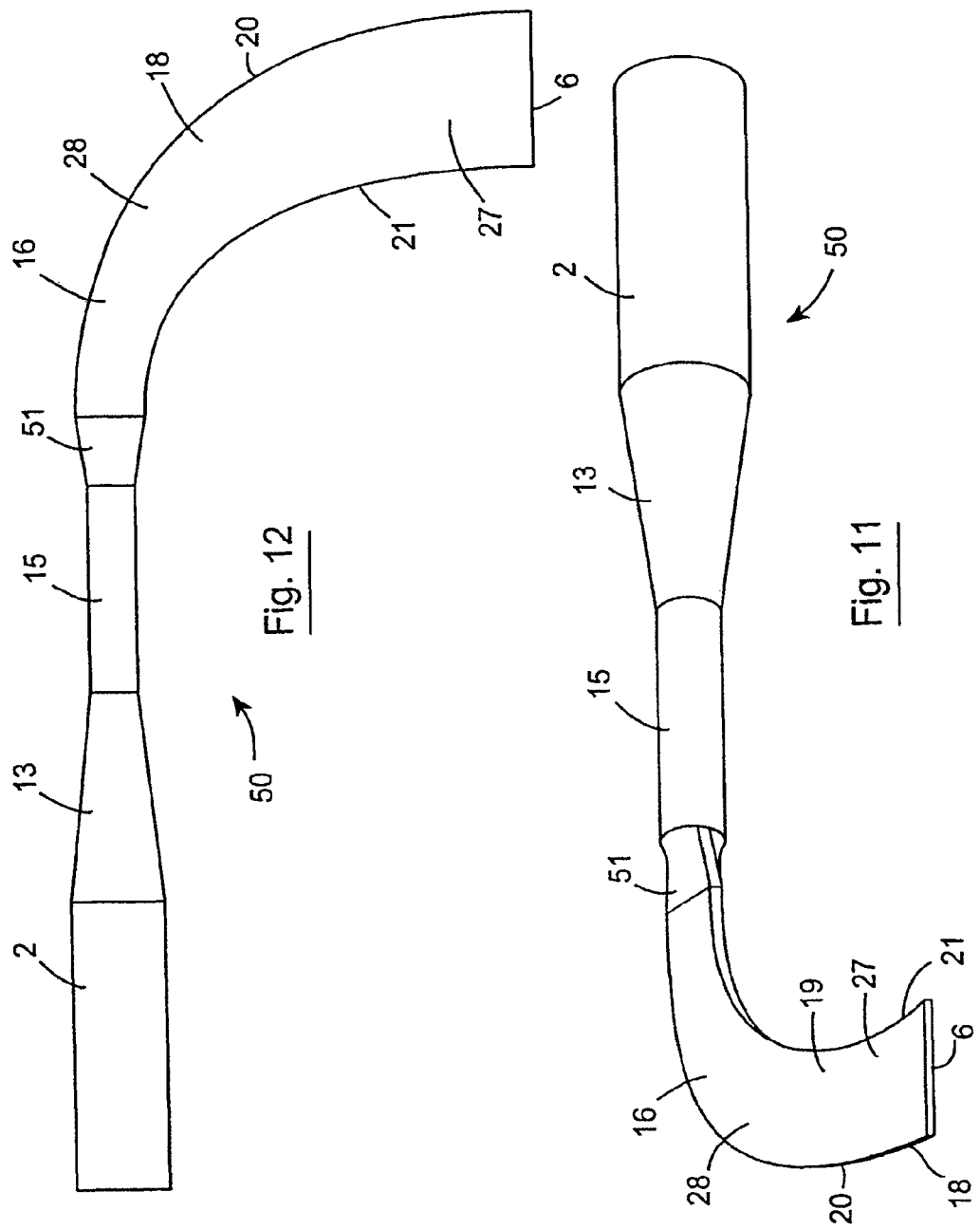

GUIDE WIRE FOR USE WITH A CATHETER

CROSS REFERENCE TO RELATED APPLICATIONS

This application is a divisional application of U.S. Ser. No. 10/567,459, filed Jul. 21, 2006, which is a 371 U.S. national phase application of PCT/IE2004/00107, filed Aug. 9, 2004, which claims priority to Irish application IE S2003/0585, filed Aug. 7, 2003.

The present invention relates to a guide wire for use in a surgical or other procedure for accessing a remote site in the body of a human or animal subject, and in particular though not limited to a guide wire for use with a catheter. The invention also relates to a method for forming a guide wire, and the invention also relates to a catheter and the guide wire in combination, and to the guide wire for accessing a remote site in the body of a human or animal subject.

Guide wires for locating a distal end of a catheter in a remote site in the body of a human or animal subject are known. Such guide wires are commonly used for guiding a catheter along narrow blood vessels to a site in the cardiovascular system of the subject for enabling cardiovascular procedures to be carried out. Typically, the guide wire is introduced through a cannula into a suitable blood vessel in the thigh or arm of the subject and is passed through the blood vessels to the desired site in the cardiovascular system. Once the guide wire has reached the desired site, the catheter is then advanced over the guide wire to the site. Guide wires are also extensively used to guide a catheter to other sites in the vascular system, and also to sites in the renal system, as well as to other sites in human and animal subjects through other systems.

Due to the relatively narrow diameter of the blood vessels through which the guide wire has to pass, and in particular, due to the tortuous nature of the blood vessels of the vascular and other systems, and the number of branching blood vessels through which the guide wire must pass, it is essential that the guide wire be of a construction which facilitates easy alignment of the guide wire with a desired one of branching blood vessels as the guide wire is being advanced through the vascular or other system, so that further urging of the guide wire results in the guide wire entering the desired branched vessel, and passing therethrough.

Various attempts have been made to provide a guide wire which can readily easily be aligned with and urged into a branching blood vessel. For example, U.S. Pat. No. 5,365,942 of Shank discloses a guide wire which comprises a core wire, the distal portion of which is flattened for facilitating manual bending of the distal portion of the guide wire by a surgeon or paramedic prior to entry of the guide wire into the body of the subject. This allows the distal portion to be bent for offsetting the distal tip of the guide wire, so that as the guide wire is being advanced through, for example, the vascular system, by rotating the guide wire the offset distal tip can be aligned with a branching blood vessel into and through which the guide wire is to be passed. Thus, further urging of the guide wire into the vascular system causes the guide wire to enter the branched vessel. In the disclosure of Shank the flattening of the distal portion of the core wire facilitates bending of the core wire out of the plane of the flattened portion. However, the flattening of the distal portion tends to reduce the column strength of the core wire, and in turn the guide wire, thus leaving the guide wire prone to buckling as it is being urged from a vessel into a branching vessel. Such buckling after the distal end has been entered into the branched vessel results in the distal end being withdrawn from the branched vessel as the guide wire is further urged into the vascular system. Additionally, such buckling can lead to kinking of the guide wire, which in general renders the guide wire unusable.

There is therefore a need for a guide wire for use in a surgical or other procedure for accessing a remote site in the body of a human or animal subject which overcomes this problem.

The present invention is directed towards providing such a guide wire, and the invention is also directed towards providing a catheter and guide wire combination, and the invention is also directed towards providing a method for forming a guide wire which overcomes the problems of prior art guide wires. The invention is further directed towards a guide wire for use in accessing a remote site in the body of a human or animal subject.

According to the invention there is provided an elongated guide wire for use in a surgical or other procedure for accessing a remote site in the body of a human or animal subject, the guide wire defining a longitudinally extending central axis, and extending axially between a distal end for accessing the remote site, and a spaced apart proximal end, a distal portion of the guide wire adjacent the distal end thereof being of substantially rectangular transverse cross-section defining a pair of spaced apart major surfaces, and a pair of spaced apart minor surfaces extending between the major surfaces, the distal portion further defining a central major plane lying intermediate the major surfaces and bisecting the minor surfaces, and a central minor plane lying intermediate the minor surfaces and bisecting the major surfaces, wherein the distal portion is bent into a curved configuration in the central major plane for forming an alignment portion lying in the central major plane and extending from the bend at an angle greater than zero relative to the central axis for facilitating guiding of the guide wire into a branched vessel of the subject.

In one embodiment of the invention the alignment portion extends relative to the central axis at an angle up to 90°.

In another embodiment of the invention the alignment portion extends relative to the central axis at an angle up to 60°.

In a further embodiment of the invention the alignment portion extends relative to the central axis at an angle up to 45°.

In a still further embodiment of the invention the alignment portion extends relative to the central axis at an angle up to 30°.

In one embodiment of the invention the alignment portion extends relative to the central axis at an angle in the range of 30° to 90°.

Preferably, the distal portion of the guide wire is of a material for retaining the distal portion in the curved configuration formed by the bend. Advantageously, the distal portion of the guide wire is of dimensions for retaining the distal portion in the curved configuration formed by the bend.

In one embodiment of the invention the distal portion of the guide wire is bendable in the central minor plane thereof for facilitating bending of the distal portion with at least a part of the alignment portion bent out of the central major plane for facilitating guiding of the guide wire into a branched vessel of the subject. Preferably, the distal portion of the guide wire is bendable in the central minor plane thereof for facilitating bending of the distal portion with the alignment portion bent out of the central major plane for facilitating guiding of the guide wire into a branched vessel of the subject.

In one embodiment of the invention the distal portion of the guide wire is of material for facilitating manual bending of the distal portion in the central minor plane thereof. Advantageously, the distal portion of the guide wire is dimensioned for facilitating manual bending of the distal portion in the central minor plane thereof.

In another embodiment of the invention the distal portion of the guide wire is of stainless steel material.

Preferably, the major surfaces of the distal portion of the guide wire converge towards the distal end. Advantageously, the minor surfaces of the distal portion of the guide wire diverge towards the distal end. Alternatively, the minor surfaces of the distal portion of the guide wire are parallel to each other.

In one embodiment of the invention a reinforcing means is provided on the distal portion of the guide wire for minimising bending of the distal portion in the central minor plane thereof. Preferably, the reinforcing means extending along at least a portion of the distal portion of the guide wire from a proximal end of the distal portion. Advantageously, the reinforcing means extends along at least a part of the alignment portion, and ideally, the reinforcing means terminates at a location spaced apart from the distal end of the alignment portion.

In one embodiment of the invention the reinforcing means is located to coincide substantially with the central minor plane defined by the distal portion.

In another embodiment of the invention the reinforcing means comprises an elongated reinforcing member extending along one of the major surfaces of the distal portion.

In one embodiment of the invention the guide wire comprises an elongated core wire extending from the proximal end to the distal portion.

In another embodiment of the invention the core wire terminates in the distal portion.

In a further embodiment of the invention the distal portion of the guide wire is integrally formed with the core wire.

Preferably, the distal portion of the guide wire is formed from the core wire. Alternatively, the distal portion of the guide wire is formed separately from the core wire, and is secured thereto.

In one embodiment of the invention the distal portion of the guide wire terminates in a bulbous portion at the distal end of the guide wire for facilitating guiding of the guide wire through vessels of the subject without damaging the vessels. Preferably, the bulbous portion is radiused. Advantageously, the bulbous portion defines the distal end of the guide wire and defines a hemispherical distal end.

In another embodiment of the invention the guide wire comprises a sleeve extending from the bulbous portion in a proximal direction and the core wire extends through the sleeve.

Preferably, the sleeve extends along the core wire in the proximal direction beyond the distal portion of the guide wire. Advantageously, the sleeve terminates at a location intermediate the distal portion and the proximal end of the guide wire.

Ideally, one end of the sleeve is secured to the bulbous portion of the guide wire, and the other end of the sleeve is secured to the core wire.

In one embodiment of the invention the sleeve is secured to the guide wire by soldering.

In another embodiment of the invention the sleeve is of transverse cross-section, the outer periphery of which substantially coincides with the outer periphery defined by the transverse cross-section of the bulbous portion.

In another embodiment of the invention the distal end of the sleeve is of a radiopaque material. Preferably, the sleeve is of a radiopaque material.

In one embodiment of the invention the sleeve is selected from one or more of the following metals:
platinum,
platinum alloy,
gold,
tantalum.

In another embodiment of the invention the sleeve comprises a helically wound coil. Preferably, the sleeve comprises a tightly wound helical coil.

Alternatively, or additionally, the sleeve is of a plastics material.

In one embodiment of the invention the sleeve is provided in at least two longitudinally extending sections, one of which is of plastics material, and the other of a tightly wound helical coil.

Additionally, the invention provides a guide wire according to the invention for use in accessing a remote site in the body of a human or animal subject.

The invention also provides in combination a catheter for use in a surgical or other procedure for accessing a remote site in the body of a human or animal subject and the elongated guide wire according to the invention.

Further the invention provides in combination a catheter for use in a surgical or other procedure for accessing a remote site in the body of a human or animal subject, and an elongated guide wire, the guide wire defining a longitudinally extending central axis, and extending axially between a distal end for accessing the remote site, and a spaced apart proximal end, a distal portion of the guide wire adjacent the distal end thereof being of substantially rectangular transverse cross-section defining a pair of spaced apart major surfaces, and a pair of spaced apart minor surfaces extending between the major surfaces, the distal portion further defining a central major plane lying intermediate the major surfaces and bisecting the minor surfaces, and a central minor plane lying intermediate the minor surfaces and bisecting the major surfaces, wherein the distal portion is bent into a curved configuration in the central major plane for forming an alignment portion lying in the central major plane and extending from the bend at an angle greater than zero relative to the central axis for facilitating guiding of the guide wire into a branched vessel of the subject.

The invention also provides a method for forming an elongated guide wire for use in a surgical or other procedure for accessing a remote site in the body of a human or animal subject, the method comprising the steps of:
  forming the distal portion of the guide wire of substantially rectangular transverse cross-section defining a pair of spaced apart major surfaces, and a pair of spaced apart minor surfaces extending between the major surfaces, the distal portion further defining a central major plane lying intermediate the major surfaces and bisecting the minor surfaces, and a central minor plane lying intermediate the minor surfaces and bisecting the major surfaces, and
  bending the distal portion into a curved configuration in the central major plane for forming an alignment portion lying in the central major plane and extending from the bend at an angle greater than zero relative to the central axis for facilitating guiding of the guide wire into a branched vessel of the subject.

The advantages of the invention are many. The guide wire according to the invention has good column strength, and in particular, has significantly greater column strength than can be provided from guide wires in which the core wire terminates in a flattened distal portion. By virtue of the fact that the distal portion is curved in the central major plane defined by the distal portion, the column strength of the guide wire is significantly enhanced. Accordingly, when the alignment portion of the distal portion is urged into a branched vessel, further urging of the guide wire into the vascular or other system causes the guide wire to be urged through the branched vessel without any danger of buckling of the guide wire.

By providing the distal portion bent to form the curvature in the central major plane, the bending of which is typically factory formed, in general, there should be no need for further bending of the distal portion by a surgeon. Accordingly, the distal portion may be provided to be of greater rectangular transverse cross-section than would otherwise be provided. However, where desired, the distal portion may be of rectangular transverse cross-section such as to permit bending of the distal portion in the central minor plane defined by the distal portion, and such bending in the central minor plane would be carried out by a surgeon or paramedic prior to the guide wire being entered into the vascular or other system of the subject. However, even where the transverse cross-section of the distal portion of the guide wire is such as to facilitate subsequent bending of the distal portion in the central minor plane defined by the distal portion, the fact that the distal portion is bent in the central major plane defined by the distal portion provides sufficient column strength to avoid buckling of the guide wire adjacent the distal portion.

Additionally, by providing the distal portion of the guide wire to be of rectangular cross-section, which is suitable for manual bending in the central minor plane defined by the distal portion, as well as the curved bend formed in the central major plane of the distal portion, the distal portion may also be subsequently manually bent in the central minor plane defined by the distal portion by a surgeon or paramedic prior to entry of the guide wire into the vascular or other system of the subject for further facilitating alignment of the alignment portion of the guide wire with a branched vessel as the guide wire is being advanced through the vascular or other system. Accordingly, the guide wire according to the invention can be provided for facilitating the forming of the alignment portion in three dimensions.

Indeed, an advantage of providing the distal portion of transverse cross-section suitable for facilitating subsequent bending of the distal portion in the central minor plane defined by the distal portion is that when the distal portion is bent in both its central major and central minor planes, the distal portion can be provided to act with a corkscrew or helical type effect as it is being urged through the vascular or other system of the subject.

Figure 4:
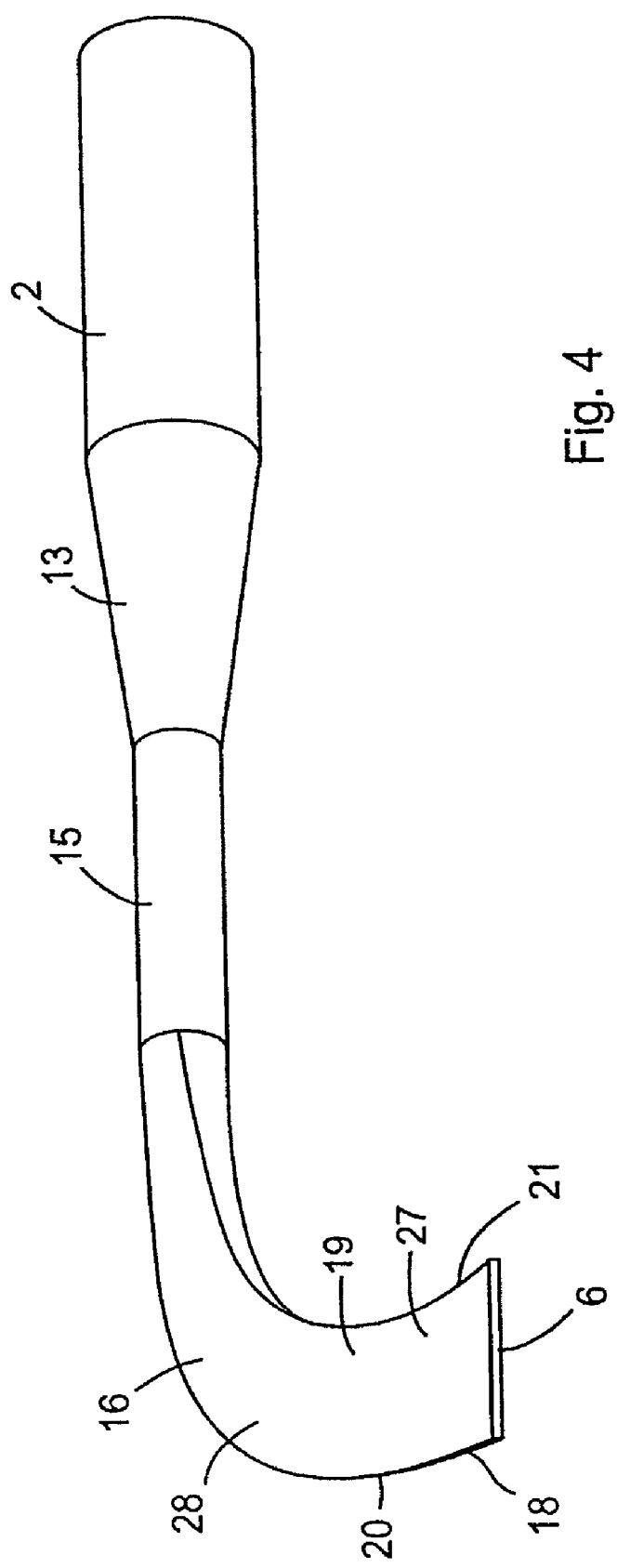
Figure 5:
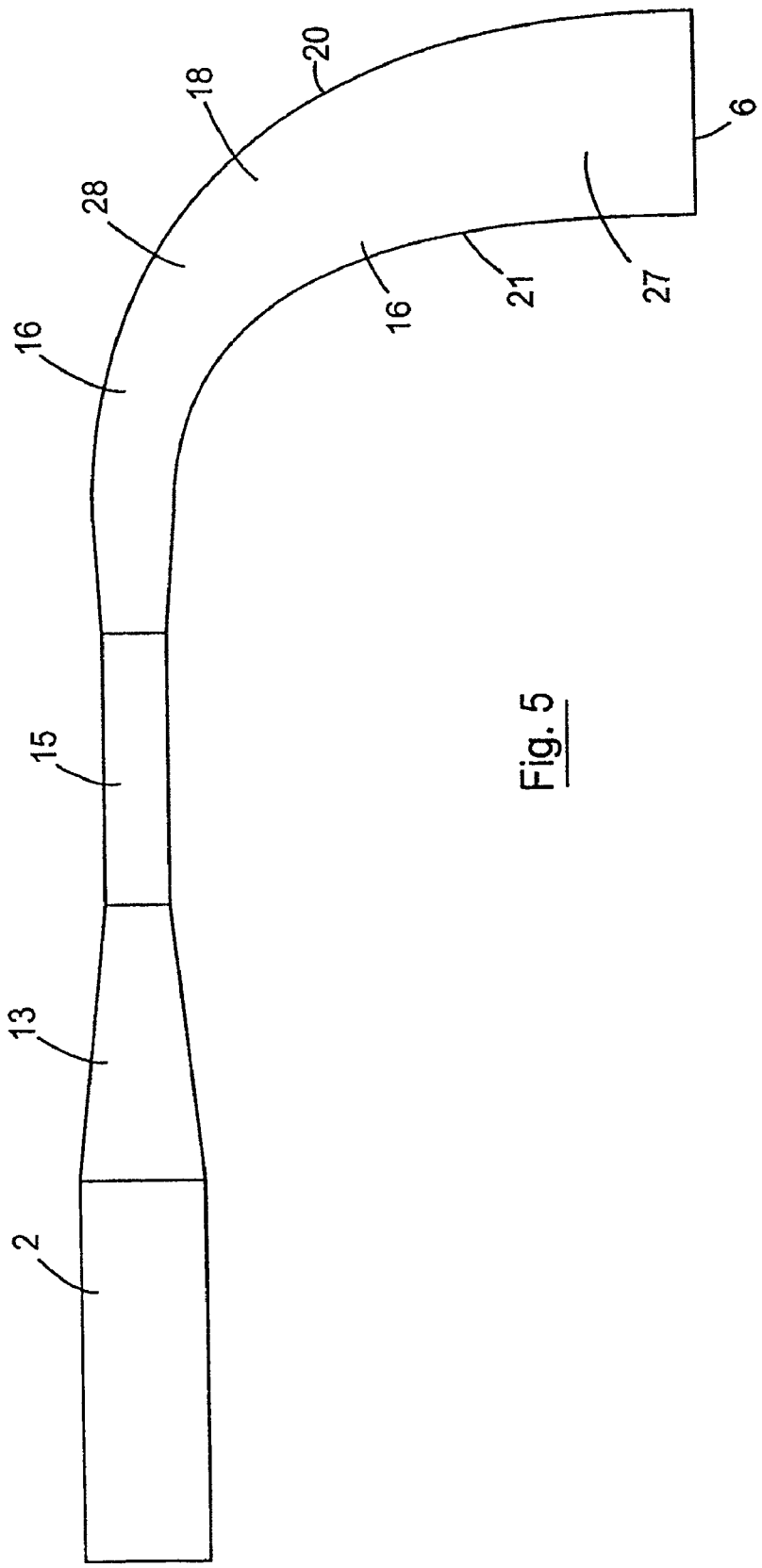
Figure 6:
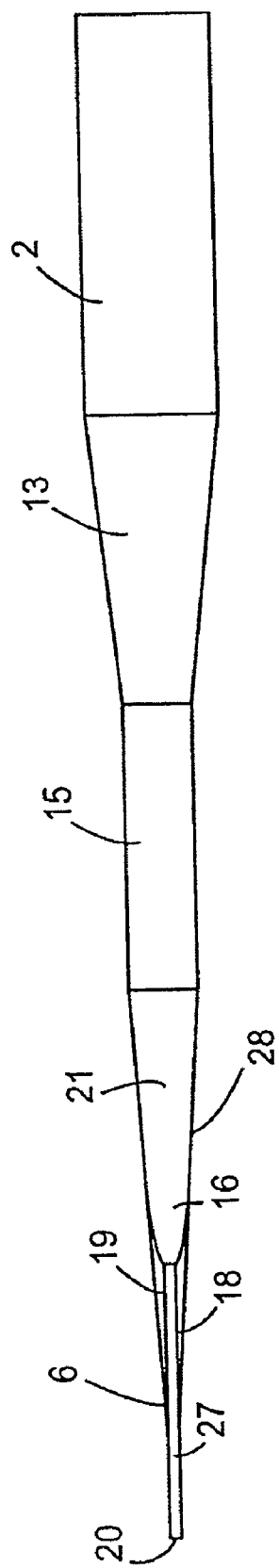
Figure 7:
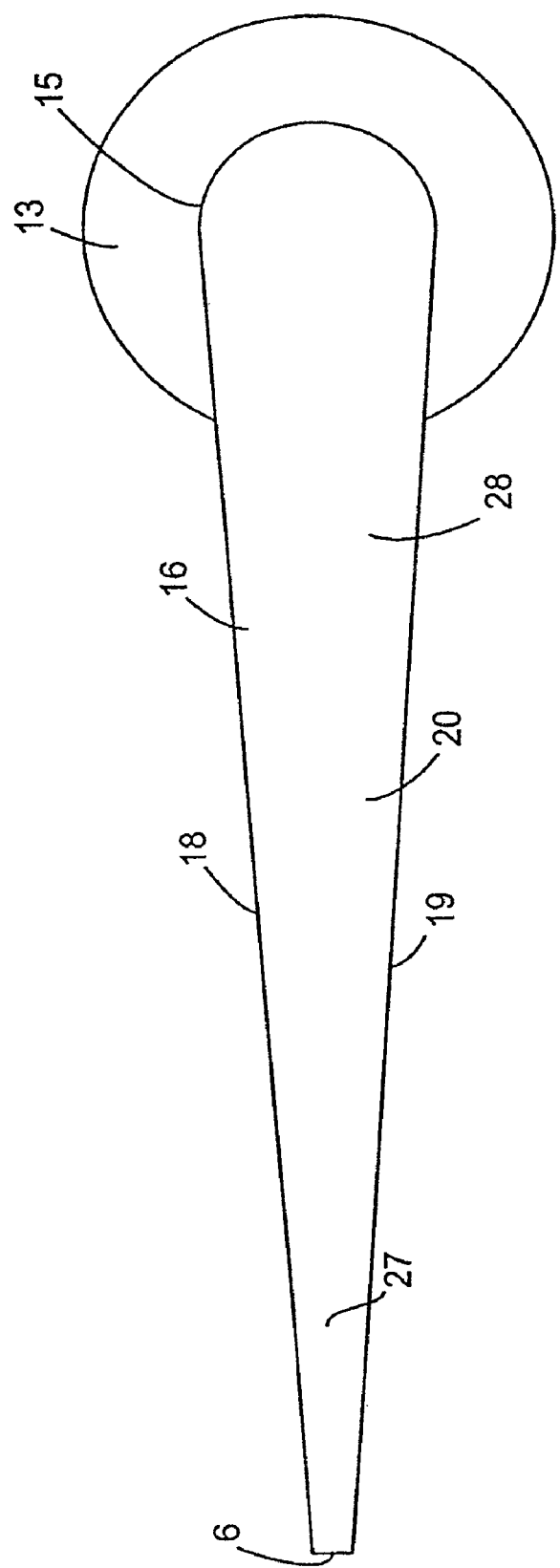
Figure 8:
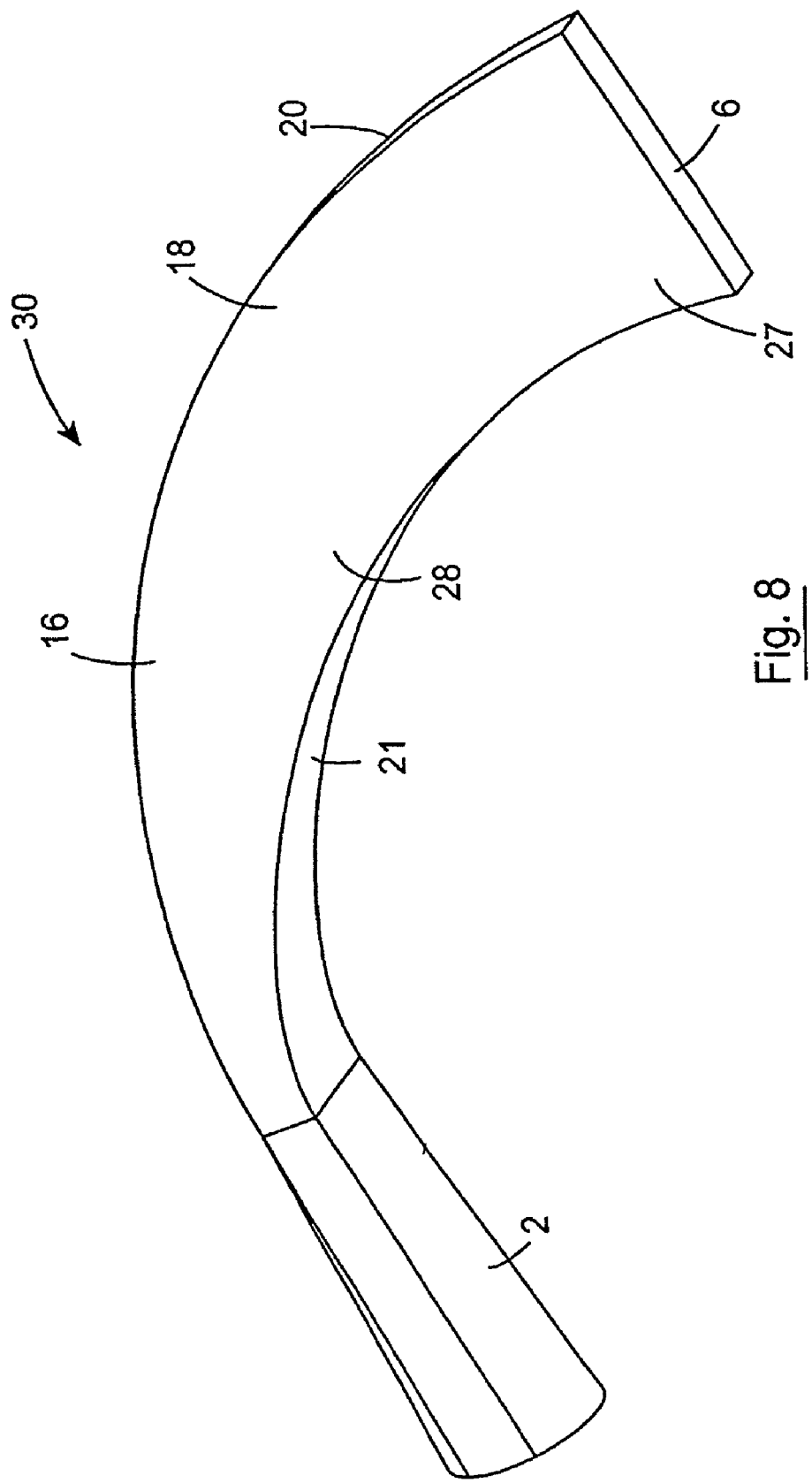
Figure 9:
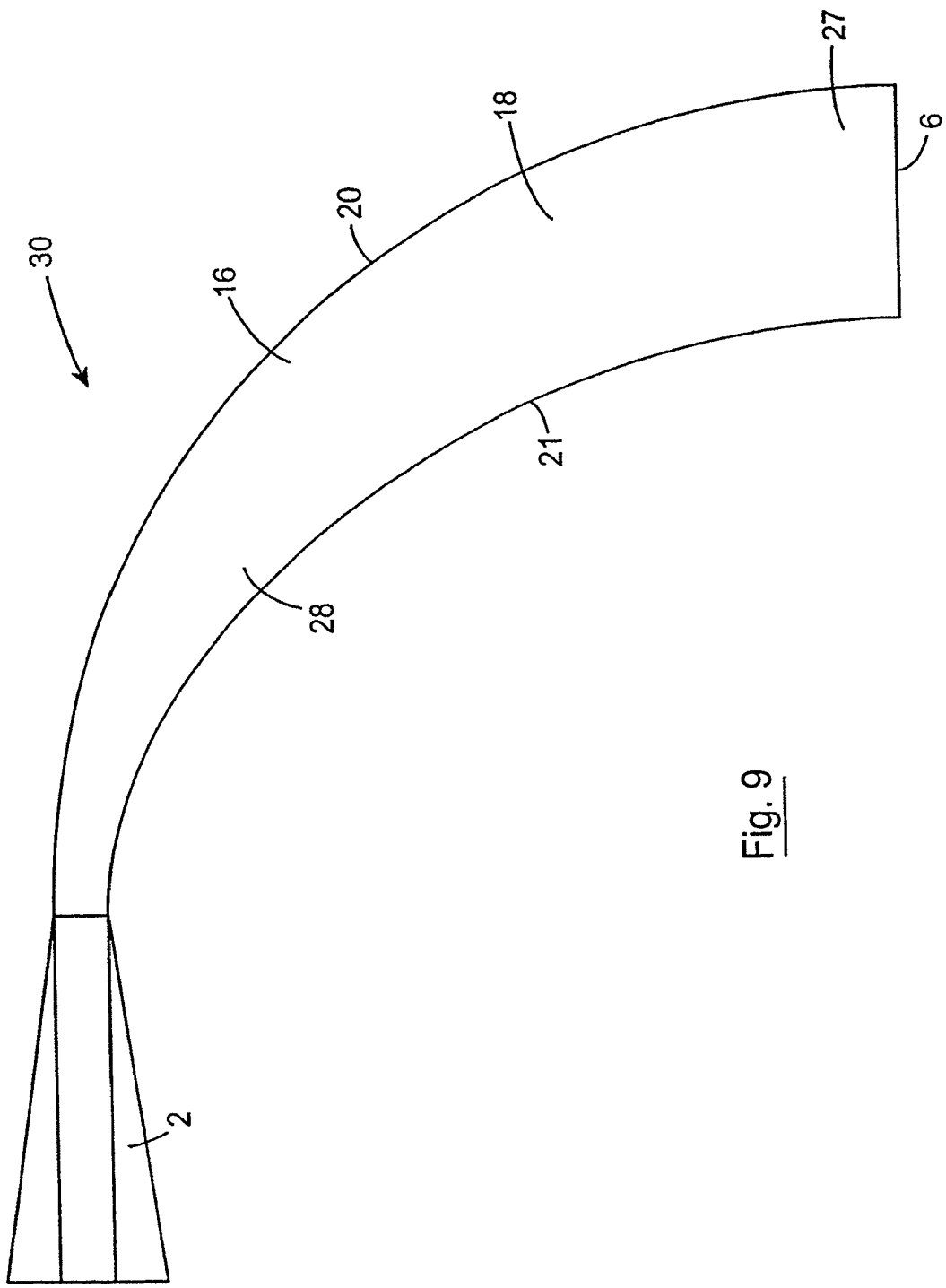
Figure 13:
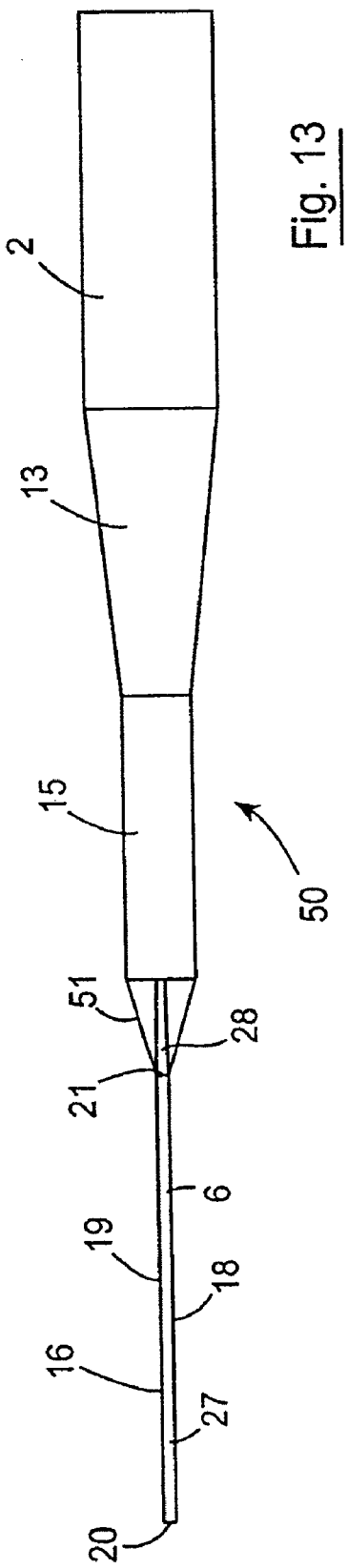
Figure 14:
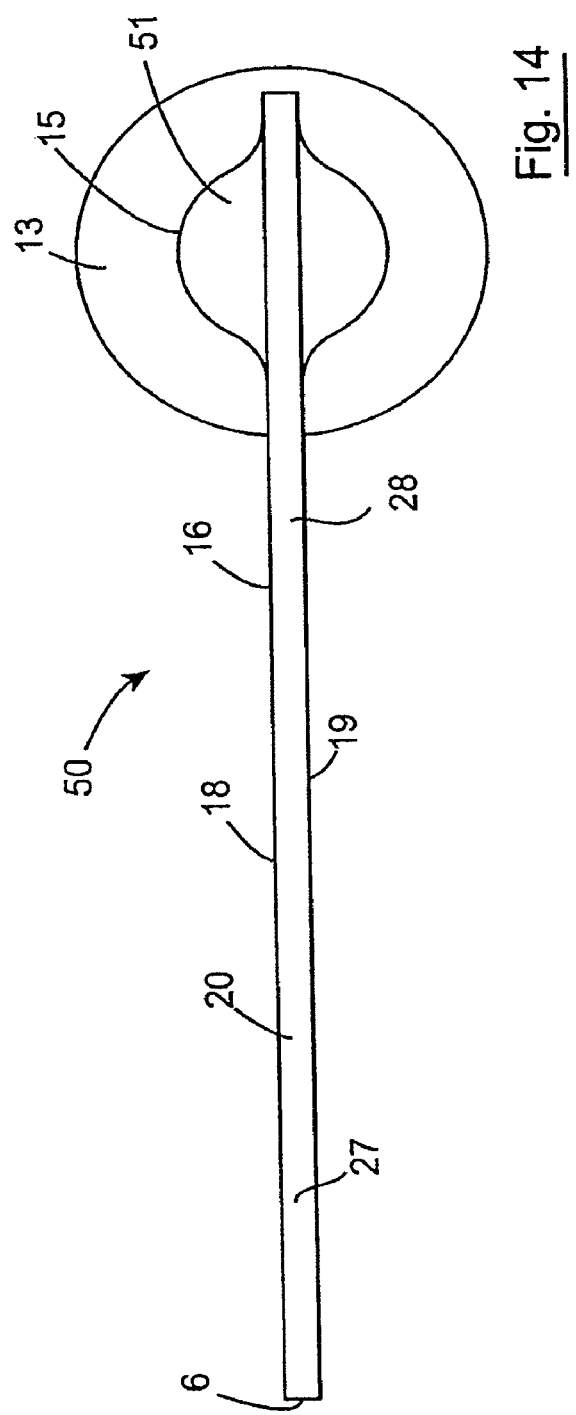

The invention will be more clearly understood from the following description of some preferred embodiments thereof, which are given by way of example only, with reference to the accompanying drawings, in which:

FIG. 1 is a partly cut-away side elevational view of a guide wire according to the invention for use with a catheter, FIG. 2 is a partly cutaway plan view of the guide wire of FIG. 1, FIG. 3 is an enlarged view of a portion of the guide wire of FIG. 1, FIG. 4 is a perspective view of a portion of the guide wire of FIG. 1, FIG. 5 is a plan view of the portion of the guide wire of FIG. 4, FIG. 6 is a side elevational view of the portion of the guide wire of FIG. 4, FIG. 7 is an end elevational view of the portion of the guide wire of FIG. 4, FIG. 8 is a perspective view of a portion of a guide wire according to another embodiment of the invention, FIG. 9 is a plan view of the portion of the guide wire of FIG. 8, FIG. 10 is a perspective view of a portion of a guide wire according to another embodiment of the invention, FIG. 11 is a perspective view similar to FIG. 4 of a portion of a guide wire according to another embodiment of the invention, FIG. 12 is a plan view of the portion of the guide wire of FIG. 11, FIG. 13 is a side elevational view of the portion of the guide wire of FIG. 11, and FIG. 14 is an end view of the portion of the guide wire of FIG. 11.

Referring to the drawings, and initially to FIGS. 1 to 7 thereof, there is illustrated a guide wire according to the invention indicated generally by the reference numeral 1 for use with a catheter (not shown) for guiding the catheter to a remote site in the body of a human or animal subject. The guide wire 1 according to this embodiment of the invention is particularly suitable for accessing a remote site in the cardiovascular system of a subject for in turn guiding the catheter (not shown) to the remote site. Although, it will be readily apparent to those skilled in the art that the guide wire 1 is suitable for accessing any remote site in the body of a human or animal subject, be it in the vascular system or otherwise. For example, the guide wire 1 is suitable for accessing a renal system, the neuro-vascular system, the fallopian tubes and other such vessels and sites.

The guide wire 1 comprises an elongated core wire 2 which in this embodiment of the invention is of stainless steel, and which defines a longitudinally extending central axis 4 and extends from a proximal end 5 to a distal end 6. The distal end 6 of the core wire 2 terminates in a bulbous portion 8 of stainless steel, which forms a hemispherical leading end for facilitating guiding of the guide wire 1 through the vascular system of the subject and for avoiding scarring, rupturing or otherwise damaging the vessels of the vascular system through which the guide wire 1 is being advanced. A sleeve 9, in this embodiment of the invention formed by a tightly wound helical coil of circular transverse cross-section, and of radiopaque material, namely, platinum alloy material, extends from the bulbous portion 8 in a proximal direction, and terminates at a location 10 on the core wire 2. The sleeve 9 is secured to the distal end 6 of the core wire 2 by solder, and the solder forms the hemispherical bulbous portion 8. Accordingly, the diameter of the bulbous portion 8 is substantially similar to the outer diameter of the sleeve 9. The sleeve 9 is also secured to the core wire 2 at the location 10 by solder.

In this embodiment of the invention, the core wire 2 is of circular transverse cross-section, and tapers in three stages 11, 12 and 13 to a portion 15 of reduced circular transverse cross-section. A distal portion 16 of the core wire 2 extends from the portion 15 to the bulbous portion 8, and is of rectangular transverse cross-section defining a pair of major surfaces 18 and 19 which are joined by a pair of minor surfaces 20 and 21. The major surfaces 18 and 19 converge from the portion 15 to the bulbous portion 8, while the minor surfaces 20 and 21 diverge from the portion 15 to the bulbous portion 8. The distal portion 16 also defines a central major plane 24 which lies intermediate the major surfaces 18 and 19 and bisects the minor surfaces 20 and 21, see FIG. 3. A central minor plane 25 is also defined by the distal portion 16, and lies intermediate the minor surfaces 20 and 21, and bisects the respective major surfaces 18 and 19.

An alignment portion 27 is pre-formed in the distal portion 16 for facilitating aligning of the distal end 6 of the guide wire 1 with a branched blood vessel as the guide wire 1 is being urged through the vascular system of the subject. The alignment portion 27 is formed by bending the distal portion 16 in the central major plane 24 to form a curved portion 28, from which the alignment portion 27 extends, so that the curved portion 28 and the alignment portion 27 along with the remainder of the distal portion 16 all lie in the central major plane 24. In this embodiment of the invention the alignment portion 27 extends from the core wire 2 at an angle θ relative to the central axis 4 of approximately 90°, although it is envisaged that the alignment portion 27 may extend from the core wire 2 at any desired angle θ relative to the central axis 4, for example, at an angle δ of 30°, 45°, 60°, or any other desired angle.

In this embodiment of the invention, the distal portion 16 is of stainless steel and is formed from the same piece of stainless steel from which the core wire 2 is formed.

The core wire 2 with the distal portion 16 is formed as follows. Initially, the core wire 2 is shaped to form the tapering stages 11, 12 and 13. The distal portion 16 is initially formed to be of diameter similar to that of the portion 15. The desired curvature is then formed in the distal portion 16 which will ultimately form the alignment portion 27, and the curved portion 28 of the distal portion 16. After the curvature has been formed in the distal portion 16, the distal portion 16 is then shaped to be of rectangular transverse cross-section with the major surfaces 18 and 19 converging towards the distal end 6, and the minor surfaces 20 and 21 diverging towards the distal end 6. After completion of the formation of the distal portion 16, the sleeve 9 is passed over the distal portion 16 and is passed along the core wire 2 to the location 10. The sleeve 9 is then soldered to the distal end 6 of the distal portion 16 to form the bulbous portion 8, and is soldered to the core wire 2 at the location 10.

The formation of the curvature in the distal portion 16 may be formed by any suitable means, for example, bending the distal portion 16 around a suitably shaped jig. The shaping of the distal portion 16 to be of rectangular transverse cross-section may be carried out by any suitable process, for example, by pressing in a suitable press tool or by the use of cam rollers.

Alternatively, the distal portion 16 may be formed separately from the core wire 2, by, for example, cutting an appropriately curved ribbon from flat stock material, and using a laser, press tool or electrochemical etch for shaping the distal portion 16 to be of the appropriate rectangular transverse cross-section. The so formed distal portion 16 would then be soldered, brazed, welded or otherwise secured to the core wire 2.

Alternatively, offset rollers may be used to create the taper and curvature in one single press where the distal portion 16 is formed integrally with the wire core 2.

In this embodiment of the invention the stainless steel material of the core wire 2 is selected, and the dimensioning and shaping of the distal portion 16 is such that the rectangular transverse cross-section of the distal portion 16 permits manual bending of the distal portion 16 in the central minor plane 25 for providing two degrees of curvature in the distal portion 16, namely, the curvature which forms the curved portion 28 of the distal portion 16 in the central major plane 24, and the curvature of the distal portion 16 in the central minor plane 25. By providing the distal portion 16 to be manually bendable in the central minor plane 25, a surgeon can manually bend the distal portion 16 in the central minor plane 25 prior to entry of the guide wire 2 into the subject, thereby providing all or a part of the alignment portion 27 bent in both the central major and central minor planes 24 and 25, thereby further facilitating alignment of the distal end 6 with a branched vessel as the guide wire 1 is being advanced through the vascular system of the subject.

While in FIGS. 1 to 7 the guide wire 1 has been described with the distal portion 16 bent in the central major plane 24, so that the alignment portion 27 extends at an angle θ of 90° to the central axis 4, it is envisaged that a set of guide wires would be provided, whereby the respective guide wires of the set would be provided with their respective alignment portions 27 extending relative to the central axis 4 at different angles θ up to 90°. Typical values of the angles θ would be 30°, 45°, 60° as well as 90°.

In use, depending on the vascular or other system of the subject to be accessed, a guide wire 1 with the distal portion 16 bent in the central major plane 24 to provide the alignment portion 27 at the desired angle θ to the central axis 4 would be selected. If appropriate, the distal portion 16 would be manually bent by the surgeon or paramedic in the central minor plane 25 in order to provide the distal portion 16, and in turn the alignment portion 27 with curvature in the central major and the central minor planes 24 and 25. After the distal portion 16 has been manually bent in the central minor plane 25, if so desired, the guide wire 1 is then ready for use, and is urged into and advanced through the vascular system of the subject in conventional fashion. When the distal end 6 of the guide wire 1 reaches a branched vessel into which the guide wire 1 is to be urged, the guide wire 1 is rotated by rotating its proximal end 5 thereof for aligning the alignment portion 27 with the branched vessel. Further urging of the guide wire 1 into the vascular system thus urges the distal end 6 of the guide wire 1 into the branched vessel, and further urging of the guide wire into the vascular system urges the guide wire 1 through the branched vessel.

Referring now to FIGS. 8 and 9, there is illustrated a portion of a guide wire according to another embodiment of the invention indicated generally by the reference numeral 30. The guide wire 30 is substantially similar to the guide wire 1, and similar components are identified by the same reference numerals. The main difference between the guide wire 30 and the guide wire 1 is that the bend forming the curved portion 28 of the distal portion 16 of the guide wire 30 is less acute than the bend forming the curved portion 28 of the distal portion 16 of the guide wire 1. Otherwise, the guide wire 30 is similar to the guide wire 1, and its use is likewise similar.

Referring now to FIG. 10, there is illustrated a portion of a guide wire according to a further embodiment of the invention, indicated generally by the reference numeral 40. The guide wire 40 is substantially similar to the guide wire 1 and similar components are identified by the same reference numerals. However, in this embodiment of the invention only half the distal portion 16 of the guide wire 40 is illustrated in FIG. 10. The distal portion 16 is bisected along the central major plane 24. The other half of the distal portion 16 is a mirror image of the illustrated portion. In this embodiment of the invention a reinforcing means provided by a reinforcing member in the form of an elongated reinforcing plate 41 extends along each major surface 18 and 19 of the distal portion 16 for increasing the column strength of the distal portion 16, and thus minimising inadvertent bending of the distal portion 16 in the central minor plane 25. The reinforcing plates 41 extend along the major surfaces 18 and 19 and coincide with the central minor plane 25 in the distal portion 16 prior to the curved portion 28. The reinforcing plates 41 may be formed integrally with the distal portion 16, or may be formed separately and welded or brazed to the distal portion 16. The advantage of providing the reinforcing plates 41 is that since the reinforcing plates 41 lie in the central minor plane 25, they act to enhance the rigidity of the distal portion 16 against bending or buckling in the central minor plane 25 as the guide wire 1 is being urged through the vascular system of the subject. Indeed, in general, it is envisaged that the reinforcing plates 41 will be of material and will be dimensioned for facilitating manual bending of the distal portion 16 in the central minor plane by a surgeon or paramedic, so that the distal portion 16 could be bent in both the central major and central minor planes 24 and 25, the bend in the central minor plane would be typically formed adjacent the distal end 6 to provide the alignment portion 27 with a type of corkscrew action. While typically the bending of the distal portion 16 in the central minor plane 25 would be carried out manually prior to use of the device by a surgeon or paramedic, it will be appreciated that bending of the distal portion in the central minor plane 25 could be carried out during manufacture of the guide wire.

Referring now to FIGS. 11 to 14, there is illustrated a portion of a guide wire according to a still further embodiment of the invention, indicated generally by the reference numeral 50. The guide wire 50 is substantially similar to the guide wire 1 and similar components are identified by the same reference numerals. The main difference between the guide wire 50 and the guide wire 1 is in the distal portion 16. In this embodiment of the invention the distal portion 16 is substantially flat, rather than tapering, as in the case of the guide wire 1. An initial tapering portion 51 rapidly tapers the core wire 2 from the portion 15 to the relatively flat distal portion 16.

Otherwise, the guide wire 50 is similar to the guide wire 1.

While the core wire, the distal portion, the bulbous portion and the sleeve of the guide wires described with reference to FIGS. 1 to 14 have been described as being of specific materials, it is envisaged that the core wire, the distal portion, the bulbous portion and the sleeve may be of any other desired or suitable materials, and in certain cases, it is envisaged that the core wire may be of nickel titanium alloy, or may be of a polymer material or a plastics material. It is also envisaged that the sleeve may be of plastics material, or portions of the sleeve may be of a plastics material. In cases where the sleeve is provided of a plastics material it is envisaged that the sleeve would be provided as a tubular sleeve.

It is also envisaged that instead of the sleeve being of radiopaque material, where it is desired to have a portion of the guide wire adjacent its distal end to be radiopaque, it is envisaged that the bulbous portion may be separately formed of a radiopaque material, for example, platinum alloy, and brazed to the core wire 2 at the distal end 6 thereof and to the sleeve.

Needless to say, the distal portion may be of a radiopaque material.

While the distal portion has been described as being of rectangular transverse cross-section, the cross-section of the distal portion may not be exactly rectangular, for example, the minor surfaces may be convex.

While the bulbous portion at the distal end of the guide wire has been described as being formed by solder of the solder joint joining the sleeve to the core wire, the bulbous portion may be formed by any other material, for example, a metal used in brazing or welding the sleeve to the core wire, or by an adhesive used in bonding the sleeve to the core wire. Alternatively, the bulbous portion could be separately formed and secured to the core wire and the sleeve by any suitable securing means, such as soldering, welding, brazing, bonding by a suitable adhesive, or the like.

As already discussed, the distal portion may be formed from the material of the core wire, or it may be formed separately of the core wire and suitably secured to the core wire after being formed. Where the distal portion is formed separately and subsequently secured to the core wire, the material of the distal portion may be the same or different to the material of the core wire.

The invention claimed is:

1. A method for forming an elongated guide wire having a central axis and a distal portion, the distal portion having a proximal end and a distal end, the method comprising the steps of:
    forming the distal portion of the guide wire of substantially rectangular transverse cross-section defining a pair of spaced apart major surfaces, and a pair of spaced apart minor surfaces extending between the major surfaces, the distal portion further defining a central major plane lying intermediate the major surfaces and bisecting the minor surfaces, and a central minor plane lying intermediate the minor surfaces and bisecting the major surfaces, the distal portion of the guide wire further having a reinforcing means for minimising bending of the distal portion in the central minor plane thereof, the reinforcing means extending along at least a portion of the distal portion of the guide wire from a proximal end of the distal portion, and
    bending the distal portion into a curved configuration to form a bend in the central major plane for forming an alignment portion lying in the central major plane and extending from the bend at an angle greater than zero relative to the central axis for facilitating guiding of the guide wire into a branched vessel of the subject.

2. A method according to claim 1 wherein the reinforcing means terminates at a location spaced apart from the distal end of the alignment portion.

3. A method according to claim 1 wherein the reinforcing means is located to coincide substantially with the central minor plane defined by the distal portion.

4. A method according to claim 1 wherein the reinforcing means is an elongated reinforcing member extending along and being perpendicular to one of the major surfaces of the distal portion.

5. A method as claimed in claim 1 in which the guide wire is formed with an elongated core wire extending from the proximal end to the distal portion, the distal portion of the guide wire being integrally formed with the core wire.

6. A method according to claim 1 wherein the guide wire is formed with an elongated core wire extending from the proximal end to the distal portion.

7. A method according to claim 1 wherein the distal portion of the guide wire is terminated in a bulbous portion at the distal end of the guide wire for facilitating guiding of the guide wire through vessels of the subject without damaging vessels.

8. A method according to claim 7 wherein a sleeve is provided extending from the bulbous portion in a proximal direction along the guide wire, and the core wire extends through the sleeve, and the sleeve terminating at a location intermediate the distal portion and the proximal end of the guide wire.

9. A method as claimed in claim 1 in which the alignment portion extends relative to the central axis at an angle in the range of 30° to 90°.

10. A method as claimed in claim 1 in which the distal portion of the guide wire is formed from a material for retaining the distal portion in the curved configuration formed by the bend.

11. A method as claimed in claim 1 in which the distal portion of the guide wire is bendable in the central minor plane thereof for facilitating bending of the distal portion with at least a part of the alignment portion bent out of the central major plane for facilitating guiding of the guide wire into a branched vessel of the subject.

12. A method according to claim 1 wherein the distal portion of the guide wire is formed from a material for facilitating manual bending of the distal portion in the central minor plane thereof.

13. A method according to claim 1 wherein the distal portion of the guide wire is formed of dimensions which facilitate manual bending of the distal portion in the central minor plane thereof.

14. A method according to claim 1 wherein the distal portion of the guide wire is formed from stainless steel.

15. A method as claimed in claim 1 in which the distal portion of the guide wire is formed with the major surfaces thereof converging towards the distal end.

16. A method as claimed in claim 1 in which the distal portion of the guide wire is formed with the minor surfaces thereof diverging towards the distal end.

* * * * *